US012665079B2

(12) United States Patent
Lyon et al.

(10) Patent No.: US 12,665,079 B2
(45) Date of Patent: Jun. 23, 2026

(54) SYSTEMS AND METHODS FOR INCREASING A SLEEPINESS OF INDIVIDUALS

(71) Applicant: ResMed Sensor Technologies Limited, Dublin (IE)

(72) Inventors: Graeme Alexander Lyon, Dublin (IE); Cesar Lopes, Dublin (IE); Michael John Costello, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 161 days.

(21) Appl. No.: 17/908,340

(22) PCT Filed: Mar. 5, 2021

(86) PCT No.: PCT/IB2021/051839
§ 371 (c)(1),
(2) Date: Aug. 31, 2022

(87) PCT Pub. No.: WO2021/176406
PCT Pub. Date: Sep. 20, 2021

(65) Prior Publication Data
US 2023/0111477 A1 Apr. 13, 2023

Related U.S. Application Data

(60) Provisional application No. 62/985,777, filed on Mar. 5, 2020.

(51) Int. Cl.
*G16H 40/63* (2018.01)
*G16H 10/60* (2018.01)
*G16H 20/30* (2018.01)

(52) U.S. Cl.
CPC ............. *G16H 40/63* (2018.01); *G16H 10/60* (2018.01); *G16H 20/30* (2018.01)

(58) Field of Classification Search
None
See application file for complete search history.

(56) References Cited

U.S. PATENT DOCUMENTS 8,348,840 B2 * 1/2013 Heit ...................... G16H 40/67
600/300
11,771,367 B1 * 10/2023 Pulkkinen .......... A61B 5/14542
705/2

(Continued)

FOREIGN PATENT DOCUMENTS

CN 103518204 A 1/2014
CN 107427665 A 12/2017

(Continued)

OTHER PUBLICATIONS

Landau, M. "Do Sleep Apps Really Work?", Consumer Reports, Feb. 2, 2019 (Year: 2019).*

(Continued)

*Primary Examiner* — Anne-Marie K Alderson
(74) *Attorney, Agent, or Firm* — NIXON PEABODY LLP

(57) ABSTRACT

A system includes a memory device storing machine-readable instructions and a control system including one or more processors configured to execute the machine-readable instructions to receive initial physiological data associated with a user, determine, based at least in part on initial physiological data, an initial sleepiness level for the user, prompt the user, via an electronic device, to perform a first activity, receive subsequent physiological data associated with the user, determine, based at least in part on the subsequent physiological data, a subsequent sleepiness level for the user, and determine a first activity score based at least in part on the initial sleepiness level and the subsequent sleepiness level, the first activity score being indicative of an effectiveness of the first activity in modifying the sleepiness of the user.

15 Claims, 7 Drawing Sheets

(56)     References Cited

U.S. PATENT DOCUMENTS

| | | | |
|---|---|---|---|
| 2010/0094103 A1 | 4/2010 | Kaplan et al. | |
| 2012/0238800 A1* | 9/2012 | Naujokat | A61B 5/4812 600/26 |
| 2014/0008837 A1 | 1/2014 | Eatherton | |
| 2014/0051942 A1* | 2/2014 | Gillette | A61B 5/372 600/483 |
| 2014/0200463 A1* | 7/2014 | el Kaliouby | A61B 5/02055 600/595 |
| 2014/0316191 A1* | 10/2014 | de Zambotti | A61B 5/486 600/27 |
| 2014/0371547 A1 | 12/2014 | Gartenberg et al. | |
| 2015/0257697 A1* | 9/2015 | Sepah | A61B 5/4815 600/300 |
| 2016/0151603 A1* | 6/2016 | Shouldice | G16H 20/70 600/26 |
| 2016/0270718 A1* | 9/2016 | Heneghan | G16H 50/20 |
| 2016/0317074 A1 | 11/2016 | Kawai et al. | |
| 2016/0367184 A1* | 12/2016 | Lim | G16H 50/30 |
| 2017/0003666 A1* | 1/2017 | Nunn | H04Q 9/00 |
| 2017/0135495 A1* | 5/2017 | Hattori | H04N 9/3179 |
| 2018/0110959 A1* | 4/2018 | Cronin | A61M 21/02 |
| 2019/0231258 A1* | 8/2019 | Lim | A61B 5/08 |
| 2019/0251858 A1 | 8/2019 | Baharav et al. | |
| 2019/0313964 A1* | 10/2019 | Ueno | A61B 5/4815 |
| 2020/0075167 A1* | 3/2020 | Srivastava | G16H 20/30 |
| 2020/0077942 A1* | 3/2020 | Youngblood | A61B 5/01 |
| 2020/0205580 A1* | 7/2020 | Sayadi | A61B 5/7475 |

FOREIGN PATENT DOCUMENTS

| | | | | | |
|---|---|---|---|---|---|
| CN | 107998500 A | 5/2018 | | | |
| JP | 2012226564 A | 11/2012 | | | |
| JP | 2013537435 A | 10/2013 | | | |
| JP | 2018512927 A | 5/2018 | | | |
| JP | 2019009742 A | 1/2019 | | | |
| WO | 2014/047310 A1 | 3/2014 | | | |
| WO | 2015/006364 A2 | 1/2015 | | | |
| WO | 2015107743 A1 | 7/2015 | | | |
| WO | 2016/061629 A1 | 4/2016 | | | |
| WO | 2017/132726 A1 | 8/2017 | | | |
| WO | 2018/050913 A1 | 3/2018 | | | |
| WO | WO-2018105459 A1 * | 6/2018 | | A61B 5/0245 |
| WO | 2019/122413 A1 | 6/2019 | | | |
| WO | 2019/122414 A1 | 6/2019 | | | |
| WO | 2020/104465 A2 | 5/2020 | | | |

OTHER PUBLICATIONS

International Search Report in International Patent Application No. PCT/IB2021/051839 mailed Aug. 2, 2021 (8 pp.).

Written Opinion in International Patent Application No. PCT/IB2021/051839 mailed Aug. 2, 2021 (11 pp.).

Feng Fan et al., "Can music improve sleep quality in adults with primary insomnia? A systematic review and network meta-analysis", International Journal of Nursing Studies, Pergamon, Amsterdam, NL, vol. 77, Oct. 23, 2017 (Oct. 23, 2017), p. 189-196; XP085308115; DOI: 10.1016/J.IJNURSTU.2017.10.011; ISSN:0020-7489.

* cited by examiner

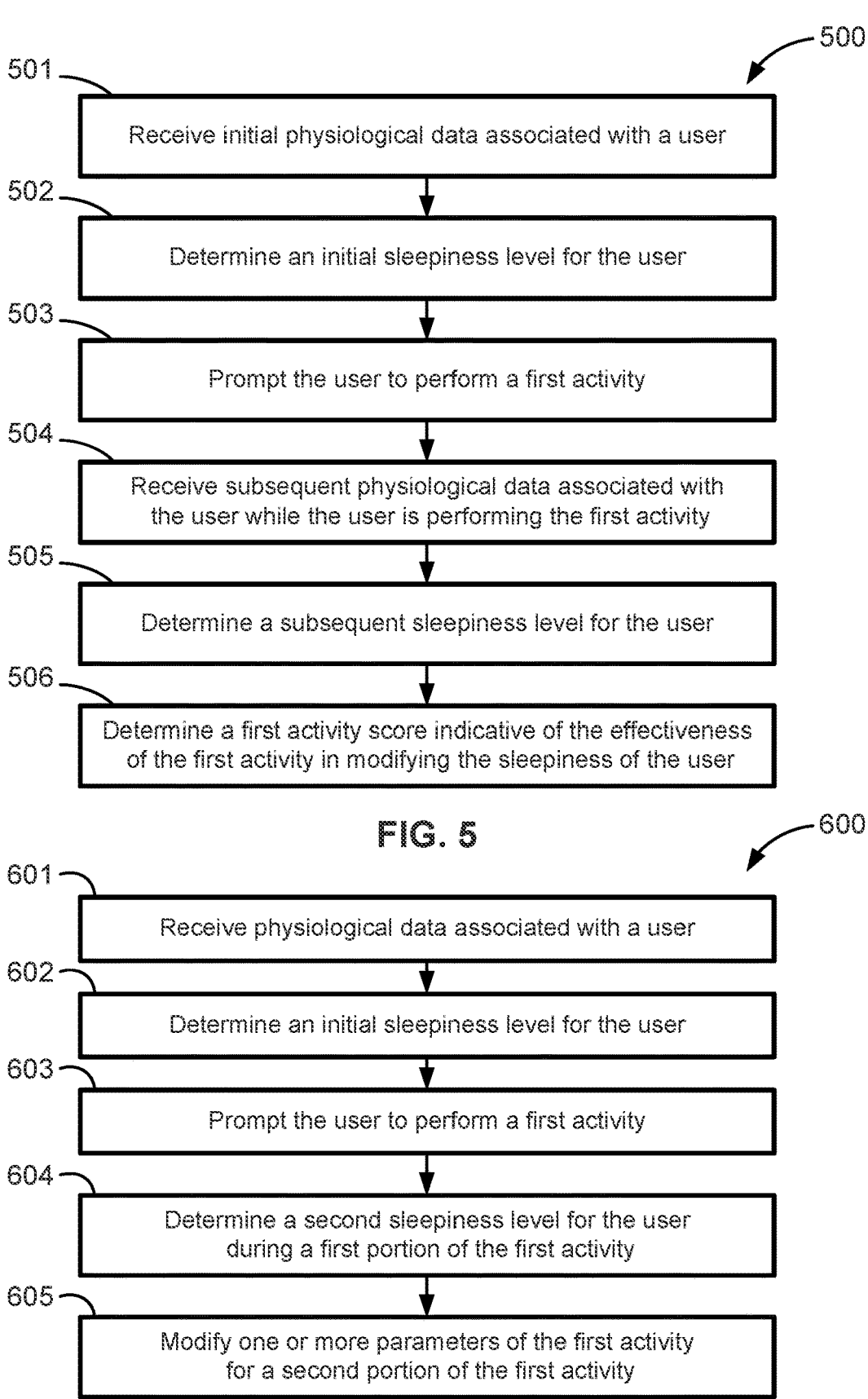

501  Receive initial physiological data associated with a user

502  Determine an initial sleepiness level for the user

503  Prompt the user to perform a first activity

504  Receive subsequent physiological data associated with the user while the user is performing the first activity 505  Determine a subsequent sleepiness level for the user 506  Determine a first activity score indicative of the effectiveness of the first activity in modifying the sleepiness of the user

FIG. 5

601  Receive physiological data associated with a user

602  Determine an initial sleepiness level for the user

603  Prompt the user to perform a first activity

604  Determine a second sleepiness level for the user during a first portion of the first activity 605  Modify one or more parameters of the first activity for a second portion of the first activity

FIG. 6

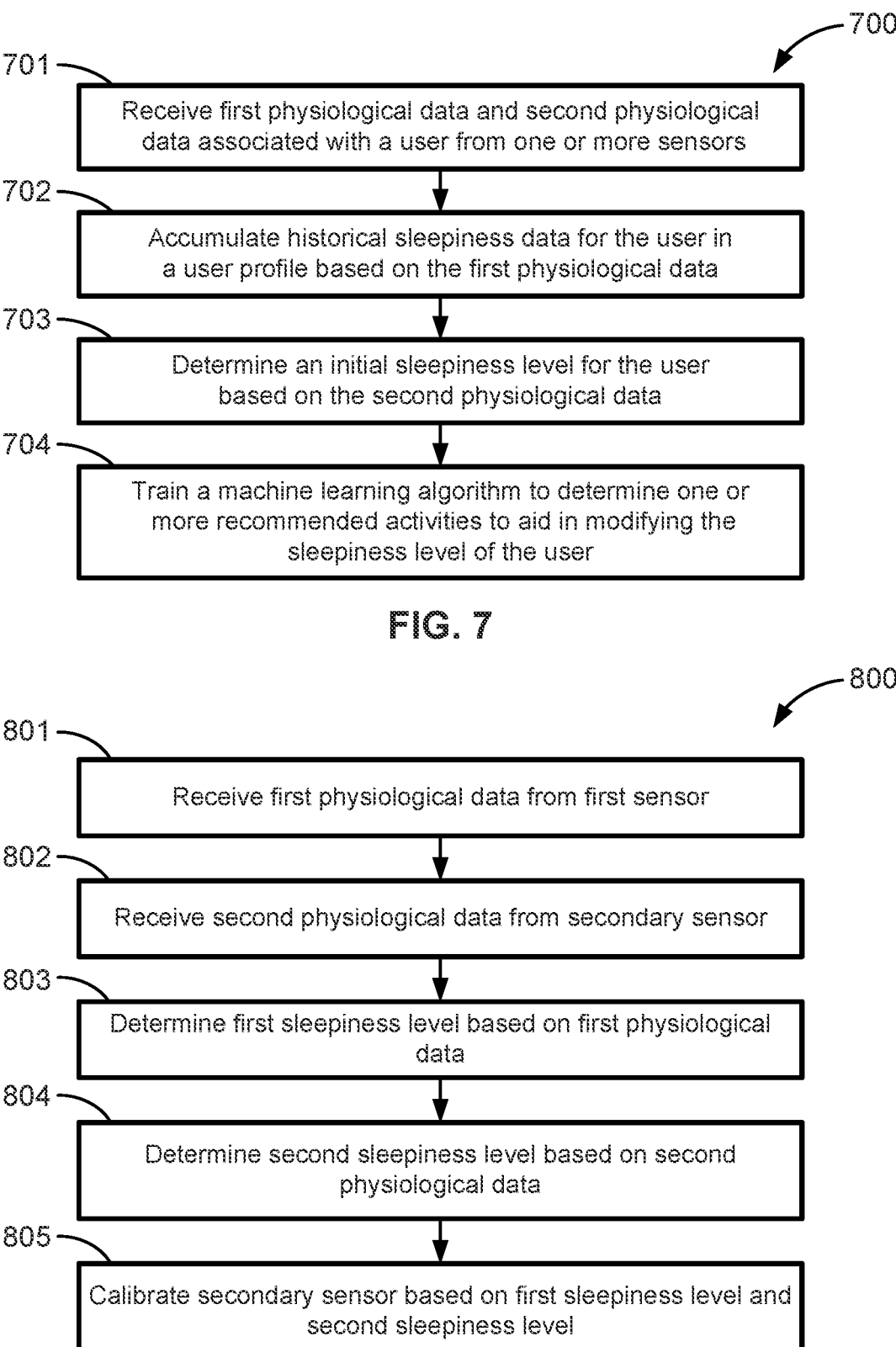

701
Receive first physiological data and second physiological data associated with a user from one or more sensors 702
Accumulate historical sleepiness data for the user in a user profile based on the first physiological data 703
Determine an initial sleepiness level for the user based on the second physiological data 704
Train a machine learning algorithm to determine one or more recommended activities to aid in modifying the sleepiness level of the user

801
Receive first physiological data from first sensor

802
Receive second physiological data from secondary sensor

803
Determine first sleepiness level based on first physiological data

804
Determine second sleepiness level based on second physiological data

805
Calibrate secondary sensor based on first sleepiness level and second sleepiness level

901 — Display media content

902 — Receive physiological data associated with a user

903 — Generate a score for the media content based at least in part on the physiological data 904 — Determine a current sleepiness level of the user 905 — Recommend media content to the user based on the current sleepiness level

900

SYSTEMS AND METHODS FOR INCREASING A SLEEPINESS OF INDIVIDUALS

CROSS-REFERENCE TO RELATED APPLICATIONS

This application is a U.S. National Stage of International Application No. PCT/IB2021/051839, filed Mar. 5, 2021, which claims the benefit of, and priority to, U.S. Provisional Patent Application Ser. No. 62/985,777, filed Mar. 5, 2020, which is hereby incorporated by reference herein in its entirety.

TECHNICAL FIELD

The present disclosure relates generally to systems and methods for monitoring insomnia and reducing insomnia-related symptoms, and more particularly, to systems and methods for identifying or recommending one or more activities that aid in increasing the sleepiness of the user and promoting sleep.

BACKGROUND

Many individuals suffer from insomnia (e.g., difficulty initiating sleep, frequent or prolonged awakenings after initially falling asleep, and an early awakening with an inability to return to sleep) or other sleep-related disorders (e.g., periodic limb movement disorder (PLMD), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), etc.). Many of these sleep related disorders can be treated or managed by prompting the user to perform one or more activities (e.g., watching media content) to aid in increase the sleepiness level of the user. Certain activities may be more effective in modifying the sleepiness level of the user than others. Thus, it would be advantageous to determine or recommend activities for an individual user that are tailored to aid in increasing the sleepiness of the user and managing insomnia symptoms. The present disclosure is directed to solving these and other problems.

SUMMARY

According to some implementations of the present disclosure, a method includes receiving initial physiological data associated with a user. The method also includes determining an initial sleepiness level for the user based at least in part on the physiological data. The method also includes prompting the user to perform a first activity. The method also includes receiving subsequent physiological data associated with the user, the subsequent physiological data being associated with the user while the user is performing the first activity, after the user has performed the activity, or both. The method also includes determining a subsequent sleepiness level for the user based at least in part on the subsequent physiological data. The method also includes determining a first activity score based at least in part on the initial sleepiness level and the subsequent sleepiness level, the first activity score being indicative of an effectiveness of the first activity in modifying the sleepiness of the user.

According to some implementations of the present disclosure, a system includes a memory storing machine-readable instructions and a control system including one or more processors configured to execute the machine-readable instructions to receive initial physiological data associated with a user, the initial physiological data being generated by a sensor. The control system is further configured to determine, based at least in part on initial physiological data, an initial sleepiness level for the user. The control system is further configured to prompt the user, via an electronic device, to perform a first activity. The control system is further configured to receive subsequent physiological data associated with the user, the subsequent physiological data being generated by the sensor while the user is performing the first activity, after the user has performed the activity, or both. The control system is further configured to determine, based at least in part on the subsequent physiological data, a subsequent sleepiness level for the user. The control system is further configured to determine a first activity score based at least in part on the initial sleepiness level and the subsequent sleepiness level, the first activity score being indicative of an effectiveness of the first activity in modifying the sleepiness of the user.

According to some implementations of the present disclosure, a method includes receiving first physiological data associated with a user. The method also includes determining an initial sleepiness level for the user based at least in part on first physiological data. The method also includes prompting the user to perform a first activity. The method also includes receiving second physiological data associated with the user, the subsequent physiological data being associated with the user while the user is performing the first activity, after the user has performed the first activity, or both. The method also includes determining a subsequent sleepiness level for the user based at least in part on the second physiological data. The method also includes determining a first activity score based at least in part on the initial sleepiness level and the subsequent sleepiness level, the first activity score being indicative of an effectiveness of the first activity in modifying the sleepiness of the user.

According to some implementations of the present disclosure, a system includes a memory storing machine-readable instructions and a control system including one or more processors configured to execute the machine-readable instructions to receive first physiological data associated with a user, the first physiological data being generated by a sensor. The control system is further configured to determine, based at least in part on first physiological data, an initial sleepiness level for the user. The control system is further configured to prompt the user, via an electronic device, to perform a first activity. The control system is further configured to receive second physiological data associated with the user, the subsequent physiological data being generated by the sensor at least while the user is performing the first activity. The control system is further configured to determine, based at least in part on the second physiological data, a subsequent sleepiness level for the user. The control system is further configured to determine a first activity score based at least in part on the initial sleepiness level and the subsequent sleepiness level, the first activity score being indicative of an effectiveness of the first activity in modifying the sleepiness of the user.

According to some implementations of the present disclosure, a method includes receiving physiological data associated with a user. The method also includes determining an initial sleepiness level for a user based at least in part on the physiological data. The method also includes prompting the user to perform a first activity using an electronic device. The method also includes determining a second sleepiness level for the user based at least in part on the physiological data responsive to the user performing a first portion of the first activity. The method also includes modifying one or more parameters of the first activity for a second portion of the first activity based at least in part on the initial sleepiness level, the second sleepiness level, or both.

According to some implementations of the present disclosure, a system includes an electronic interface, a memory, and a control system. The electronic interface is configured to receive physiological data associated with a user, the physiological data being generated by one or more sensors. The memory stores machine-readable instructions. The control system includes one or more processors configured to execute the machine-readable instructions to determine, based at least in part on the physiological data, an initial sleepiness level for a user. The control system is further configured to prompt the user to perform a first activity using an electronic device, responsive to the user performing a first portion of the first activity. The control system is further configured to determine, based at least in part on the physiological data, a second sleepiness level for the user. The control system is further configured to modify one or more parameters of the first activity for a second portion of the first activity based at least in part on the initial sleepiness level, the second sleepiness level, or both.

According to some implementations of the present disclosure, a method includes receiving first physiological data associated with a user. The method also includes accumulating, in a user profile associated with the user, historical sleepiness data for the user including a set of previously recorded changes in sleepiness level for the user, each one of the changes in sleepiness level in the set of previously recorded changes in sleepiness level being associated with a corresponding one of a plurality of activities, the historical sleepiness data being based at least in part on the first physiological data. The method also includes receiving second physiological data associated with the user. The method also includes determining, based at least in part on the second physiological data generated by the second sensor, an initial sleepiness level for the user. The method also includes training a machine learning algorithm using the user profile such that the machine learning algorithm is configured to (i) receive as an input the initial sleepiness level of the user and (ii) determine as an output one or more recommended activities from the plurality of activities to aid in modifying the sleepiness level of the user relative to the initial sleepiness level.

According to some implementations of the present disclosure, a system includes an electronic interface, a memory, and a control system. The electronic interface is configured to receive (i) first physiological data associated with a user and (ii) second physiological data associated with the user, the first physiological data and the second physiological data being generated by one or more sensors. The memory stores machine-readable instructions. The control system includes one or more processors configured to execute the machine-readable instructions to accumulate, in a user profile associated with the user, historical sleepiness data for the user including a set of previously recorded changes in sleepiness level for the user, each one of the changes in sleepiness level in the set of previously recorded changes in sleepiness level being associated with a corresponding one of a plurality of activities, the historical sleepiness data being based at least in part on the first physiological data generated by the first sensor. The control system is further configured to determine, based at least in part on the second physiological data generated by the second sensor, an initial sleepiness level for a user. The control system is further configured to train a machine learning algorithm using the user profile such that the machine learning algorithm is configured to (i) receive as an input the initial sleepiness level of the user and (ii) determine as an output one or more recommended activities from the plurality of activities to aid in modifying the sleepiness level of the user relative to the initial sleepiness level.

According to some implementations of the present disclosure, a method includes generating first physiological data associated with a user during a first period using a first sensor, generating second physiological data associated with the user during the first period using a secondary sensor. The method also includes determining, by a control system, a first sleepiness level of the user based on the first physiological data generated by the first sensor. The method also includes determining, by the control system, a second sleepiness level of the user based on the second physiological data generated by the secondary sensor. The method also includes calibrating the secondary sensor such that the determined second sleepiness level matches the determined first sleepiness level.

According to some implementations of the present disclosure, a method includes receiving data associated with a user while the user is viewing a plurality of media content segments. The method also includes generating a score for each of the plurality of media content segments based at least in part on the received data, the score being indicative of a change in a sleepiness level of the user. The method also includes determining a current sleepiness level of the user. The method also includes recommending, based at least in part on the current sleepiness level of the user and the generated scores, one or of more of the plurality of media content segments to the user to aid in changing the current sleepiness level of the user.

According to some implementations of the present disclosure, a system includes a display device, a sensor, a memory, and a control system. The display device is configured to display a plurality of media content segments. The sensor is configured to generate data associated with a user while the user views each of the plurality of media content segments. The memory stores machine-readable instructions. The control system includes one or more processors configured to execute the machine-readable instructions to, for each of the plurality of media content segments, generate a score that is based at least in part on the generated data associated with the user, the score being indicative of a change in a sleepiness level of the user. The controls system is further configured to determine a current sleepiness level of the user. The control system is further configured to, based at least in part on the current sleepiness level of the user, recommend one or of more of the plurality of media content segments to aid in changing the current sleepiness level of the user.

According to some implementations of the present disclosure, a system includes a display device configured to display media content, a sensor configured to generate data associated with a user while the user views the media content, a memory storing machine-readable instructions, and a control system including one or more processors configured to execute the machine-readable instructions to accumulate historical scores for each of a plurality of segments of the media content based at least in part on the generated data associated with the user, each of the historical scores being indicative of a change in a sleepiness level of the user. The control system is further configured to determine a current sleepiness level of the user. The control system is further configured to train a machine learning algorithm based at least in part on the historical scores such that the machine learning algorithm is configured to receive as an input the current sleepiness level of the user and output one or more recommended segments from the plurality of segments of media content to aid in changing the current sleepiness level of the user.

The above summary is not intended to represent each implementation or every aspect of the present disclosure. Additional features and benefits of the present disclosure are apparent from the detailed description and figures set forth below.

BRIEF DESCRIPTION OF THE DRAWINGS

FIG. 5 is a process flow diagram for a method of determining an activity score that is indicative of the effectiveness of an activity in modifying the sleepiness of the user, according to some implementations of the present disclosure;

FIG. 6 is a process flow diagram for a method of modifying one or more parameters of an activity, according to some implementations of the present disclosure;

FIG. 7 is a process flow diagram for determining one or more recommended activities to aid in modifying a sleepiness level of the user;

FIG. 8 for calibrating a sensor for determining a sleepiness level of a user, according to some implementations of the present disclosure.

Figure 1:
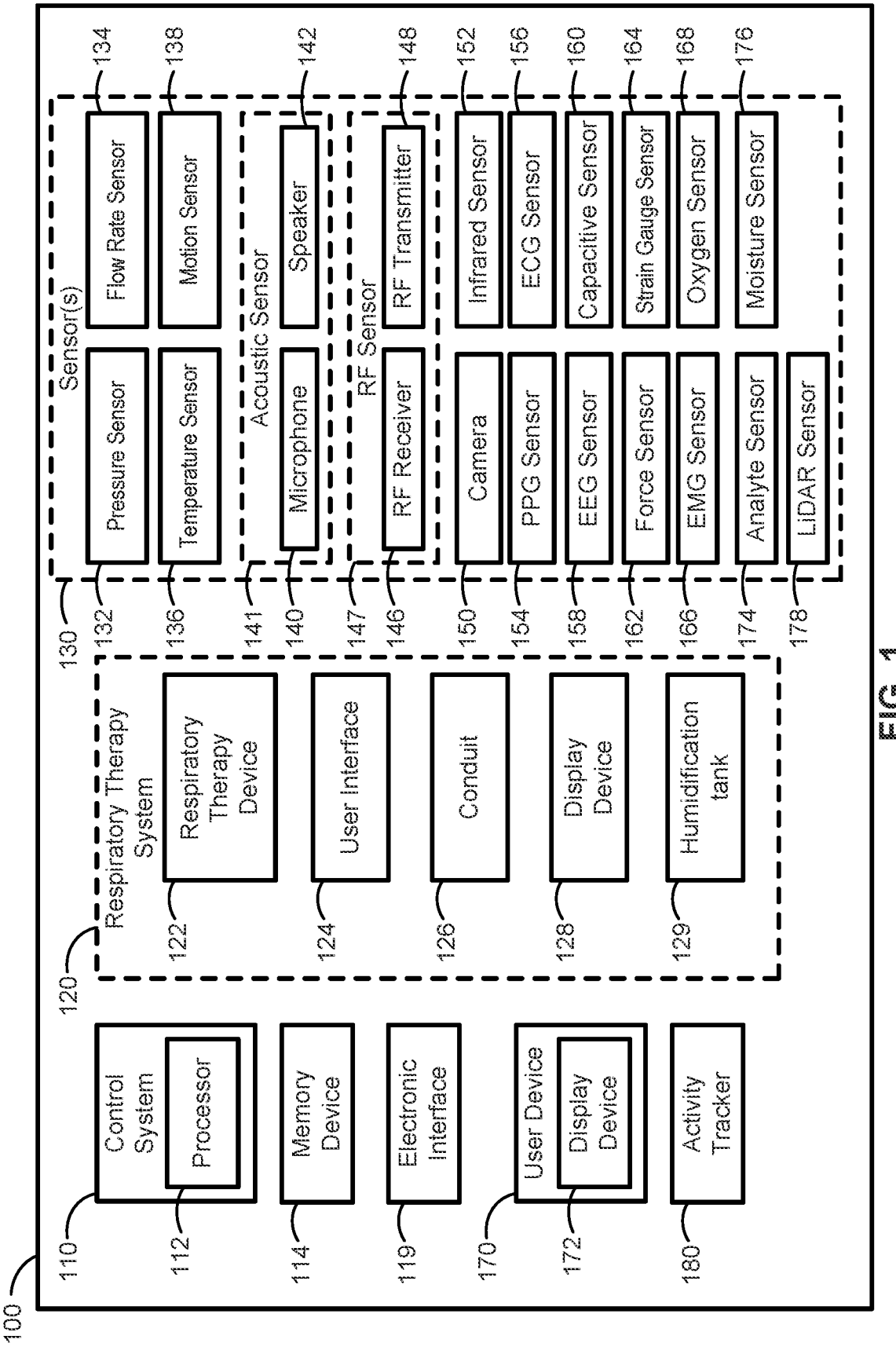
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from insomnia, a condition which is generally characterized by a dissatisfaction with sleep quality or duration (e.g., difficulty initiating sleep, frequent or prolonged awakenings after initially falling asleep, and an early awakening with an inability to return to sleep). It is estimated that over 2.6 billion people worldwide experience some form of insomnia, and over 750 million people worldwide suffer from a diagnosed insomnia disorder. In the United States, insomnia causes an estimated gross economic burden of $107.5 billion per year, and accounts for 13.6% of all days out of role and 4.6% of injuries requiring medical attention. Recent research also shows that insomnia is the second most prevalent mental disorder, and that insomnia is a primary risk factor for depression.

Nocturnal insomnia symptoms generally include, for example, reduced sleep quality, reduced sleep duration, sleep-onset insomnia, sleep-maintenance insomnia, late insomnia, mixed insomnia, and/or paradoxical insomnia. Sleep-onset insomnia is characterized by difficulty initiating sleep at bedtime. Sleep-maintenance insomnia is characterized by frequent and/or prolonged awakenings during the night after initially falling asleep. Late insomnia is characterized by an early morning awakening (e.g., prior to a target or desired wakeup time) with the inability to go back to sleep. Comorbid insomnia refers to a type of insomnia where the insomnia symptoms are caused at least in part by a symptom or complication of another physical or mental condition (e.g., anxiety, depression, medical conditions, and/or medication usage). Mixed insomnia refers to a combination of attributes of other types of insomnia (e.g., a combination of sleep-onset, sleep-maintenance, and late insomnia symptoms). Paradoxical insomnia refers to a disconnect or disparity between the user's perceived sleep quality and the user's actual sleep quality.

Diurnal (e.g., daytime) insomnia symptoms include, for example, fatigue, reduced energy, impaired cognition (e.g., attention, concentration, and/or memory), difficulty functioning in academic or occupational settings, and/or mood disturbances. These symptoms can lead to psychological complications such as, for example, lower performance, decreased reaction time, increased risk of depression, and/or increased risk of anxiety disorders. Insomnia symptoms can also lead to physiological complications such as, for example, poor immune system function, high blood pressure, increased risk of heart disease, increased risk of diabetes, weight gain, and/or obesity.

Insomnia can also be categorized based on its duration. For example, insomnia symptoms are typically considered acute or transient if they occur for less than 3 months. Conversely, insomnia symptoms are typically considered chronic or persistent if they occur for 3 months or more, for example. Persistent/chronic insomnia symptoms often require a different treatment path than acute/transient insomnia symptoms.

Mechanisms of insomnia include predisposing factors, precipitating factors, and perpetuating factors. Predisposing factors include hyperarousal, which is characterized by increased physiological arousal during sleep and wakefulness. Measures of hyperarousal include, for example, increased levels of cortisol, increased activity of the autonomic nervous system (e.g., as indicated by increase resting heart rate and/or altered heart rate), increased brain activity (e.g., increased EEG frequencies during sleep and/or increased number of arousals during REM sleep), increased metabolic rate, increased body temperature and/or increased activity in the pituitary-adrenal axis. Precipitating factors include stressful life events (e.g., related to employment or education, relationships, etc.) Perpetuating factors include excessive worrying about sleep loss and the resulting consequences, which may maintain insomnia symptoms even after the precipitating factor has been removed.

Once diagnosed, insomnia can be managed or treated using a variety of techniques or providing recommendations to the patient. As described herein, insomnia can be managed or treated by prompting an individual perform one or more activities before bed to modify (e.g., increase) the sleepiness of the individual to aid in causing the individual to fall asleep. Generally, the patient can be encouraged or recommended to generally practice healthy sleep habits (e.g., plenty of exercise and daytime activity, have a routine, no bed during the day, eat dinner early, relax before bedtime, avoid caffeine in the afternoon, avoid alcohol, make bedroom comfortable, remove bedroom distractions, get out of bed if not sleepy, try to wake up at the same time each day regardless of bed time) or discouraged from certain habits (e.g., do not work in bed, do not go to bed too early, do not go to bed if not tired). An individual suffering from insomnia can be treated by improving the sleep hygiene of the individual. Sleep hygiene generally refers to the individual's practices (e.g., diet, exercise, substance use, bedtime, activities before going to sleep, activities in bed before going to sleep, etc.) and/or environmental parameters (e.g., ambient light, ambient noise, ambient temperature, etc.). In at least some cases, the individual can improve their sleep hygiene by going to bed at a certain bedtime each night, sleeping for a certain duration, waking up at a certain time, modifying the environmental parameters, or any combination thereof.

Examples of sleep-related and/or respiratory disorders include Periodic Limb Movement Disorder (PLMD), Restless Leg Syndrome (RLS), Sleep-Disordered Breathing (SDB), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood. Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness. Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping. While these other sleep-related disorders may have similar symptoms as insomnia, distinguishing these other sleep-related disorders from insomnia is useful for tailoring an effective treatment plan distinguishing characteristics that may call for different treatments. For example, fatigue is generally a feature of insomnia, whereas excessive daytime sleepiness is a characteristic feature of other disorders (e.g., OSA) and reflects a physiological propensity to fall asleep unintentionally.

Referring to FIG. 1, a system 100, according to some implementations of the present disclosure, is illustrated. The system 100 includes a control system 110, a memory device 114, an electronic interface 119, one or more sensors 130, and one or more user devices 170. In some implementation, the system 100 further optionally includes a respiratory therapy system 120.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120. The respiratory therapy system 120 can include a respiratory pressure therapy device 122 (referred to herein as respiratory therapy device 122), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
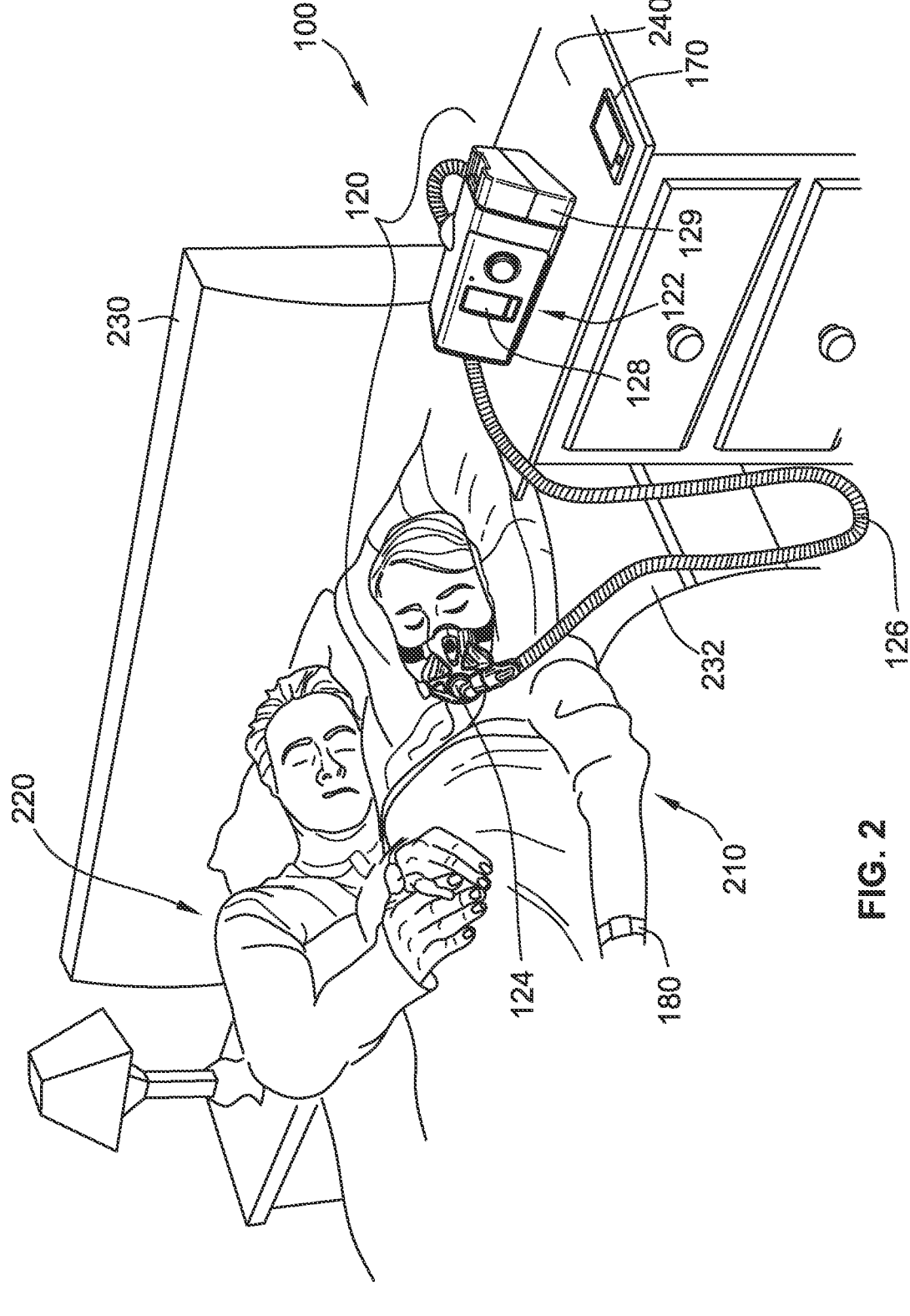
FIG. 2 is a perspective view of at least a portion of the system of FIG. 1, a user, and a bed partner, according to some implementations of the present disclosure.

As shown in FIG. 2, in some implementations, the user interface 124 is a facial mask that covers the nose and mouth of the user. Alternatively, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 includes a mouthpiece (e.g., a night guard mouthpiece molded to conform to the user's teeth, a mandibular repositioning device (MRD), etc.).

The conduit 126 (also referred to as an air circuit or tube) allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be use, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score and/or a therapy score (also referred to as a myAir™ score, such as described in International Publication No. WO 2016/061629, which is hereby incorporated by reference herein in its entirety), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user.

The respiratory therapy system 120 can be used, for example, as a positive airway pressure (PAP) system, a continuous positive airway pressure (CPAP) system, an automatic positive airway pressure system (APAP), a bi-level or variable positive airway pressure system (BPAP or VPAP), a ventilator, or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a LiDAR sensor 178, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, or sleep stages, such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more of the sensors, such as sensors 130, are described in, for example, International Publication Nos. WO 2014/047310, WO 2017/132726, WO 2019/122413, and WO 2019/122414 and U.S. Patent Publication No. US 2014/0088373, each of which is hereby incorporated by reference herein in its entirety.

The sleep-wake signal can also be timestamped to indicate a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 122, or any combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. In some implementations, the one or more sleep-related parameters can include a sleep score, such as the ones described in International Publication No. WO 2015/006364, which is hereby incorporated by reference herein in its entirety.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, a piezoelectric sensor, a strain-gauge sensor, an optical sensor, a potentiometric sensor, or any combination thereof.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The microphone 140 outputs sound data that can be stored in the memory device 114 and/or analyzed by the processor 112 of the control system 110. The microphone 140 can be used to record sound(s) during a sleep session (e.g., sounds from the user 210) to determine (e.g., using the control system 110) one or more sleep-related parameters, as described in further detail herein. The microphone 140 can be coupled to or integrated in the respiratory therapy device 122, the use interface 124, the conduit 126, or the user device 170.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a sonar sensor), as described in, for example, WO 2018/050913 and WO 2020/104465, each of which is hereby incorporated by reference herein in its entirety. In such implementations, the speaker 142 generates or emits sound waves at a predetermined interval and/or frequency and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, pressure settings of the respiratory device 122, a type of movement of the user (e.g., movement of one or more portions of the user, chest movement, etc.), a pattern of movement by the user, a number of movements by the user, or any combination thereof.

The acoustic (e.g., sonar) sensor 141 can use passive and/or active acoustic sensing, such as by generating/transmitting ultrasound or low frequency ultrasound sensing signals (e.g., in a frequency range of about 17-23 kHz, 18-22 kHz, or 17-18 kHz, for example) through the air. Such sonar sensors are described in relation to WO 2018/050913 and WO 2020/104465 referenced above. Data generated by the acoustic (e.g., sonar) sensor 141 can be indicative of respiration of the user (e.g., respiration rate, respiration rate variability) and/or movement of the user, which can be used, for example, to determine a transition between wakefulness and the non-REM sleep stage (N1 sleep). N1 sleep can be identified based at least in part on a decrease in respiration rate variability (e.g., breathing is becoming more regular), a decrease in minute ventilation, and/or less movement of the user.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a radar sensor). In some such implementations, the RF sensor 147 includes a control circuit. The specific format of the RF communication can be WiFi, Bluetooth, or the like.

In some implementations, the RF sensor 147 is a part of a mesh system. One example of a mesh system is a WiFi mesh system, which can include mesh nodes, mesh router (s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based on changes in the WiFi signals (e.g., differences in received signal strength) between the router and the satellite (s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user 210 enters the bed 230 (FIG. 2), and to determine a time when the user 210 exits the bed 230.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory therapy device 122, etc.). Thus, in some implementations, the moisture sensor 176 can be coupled to or integrated in the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 166 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such as glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, or any combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, at least one of the one or more sensors 130 is not coupled to the respiratory therapy device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The user device 170 (FIG. 1) includes a display device 172. The user device 170 can be, for example, a mobile device such as a smart phone, a tablet, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

In some implementations, the system 100 also includes an activity tracker 180. The activity tracker 180 is generally used to aid in generating physiological data associated with the user. The activity tracker 180 can include one or more of the sensors 130 described herein, such as, for example, the motion sensor 138 (e.g., one or more accelerometers and/or gyroscopes), the PPG sensor 154, and/or the ECG sensor 156. The physiological data from the activity tracker 180 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum he respiration art rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the activity tracker 180 is coupled (e.g., electronically or physically) to the user device 170.

In some implementations, the activity tracker 180 is a wearable device that can be worn by the user, such as a smartwatch, a wristband, a ring, or a patch. For example, referring to FIG. 2, the activity tracker 180 is worn on a wrist of the user 210. The activity tracker 180 can also be coupled to or integrated a garment or clothing that is worn by the user. Alternatively still, the activity tracker 180 can also be coupled to or integrated in (e.g., within the same housing) the user device 170. More generally, the activity tracker 180 can be communicatively coupled with, or physically integrated in (e.g., within a housing), the control system 110, the memory 114, the respiratory system 120, and/or the user device 170.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc.), or any combination thereof.

While system 100 is shown as including all of the components described above, more or fewer components can be included in a system for generating physiological data and determining a recommended notification or action for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. Thus, various systems can be formed using any portion or portions of the components shown and described herein and/or in combination with one or more other components.

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

Figure 3:
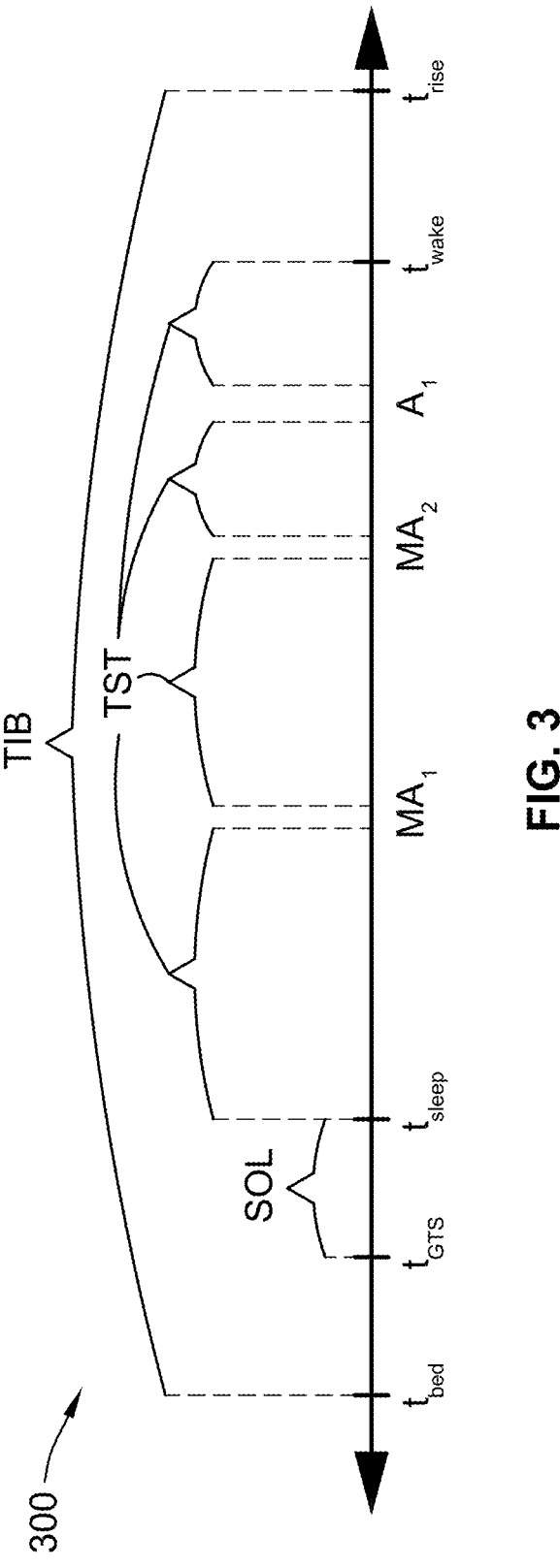
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TM).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
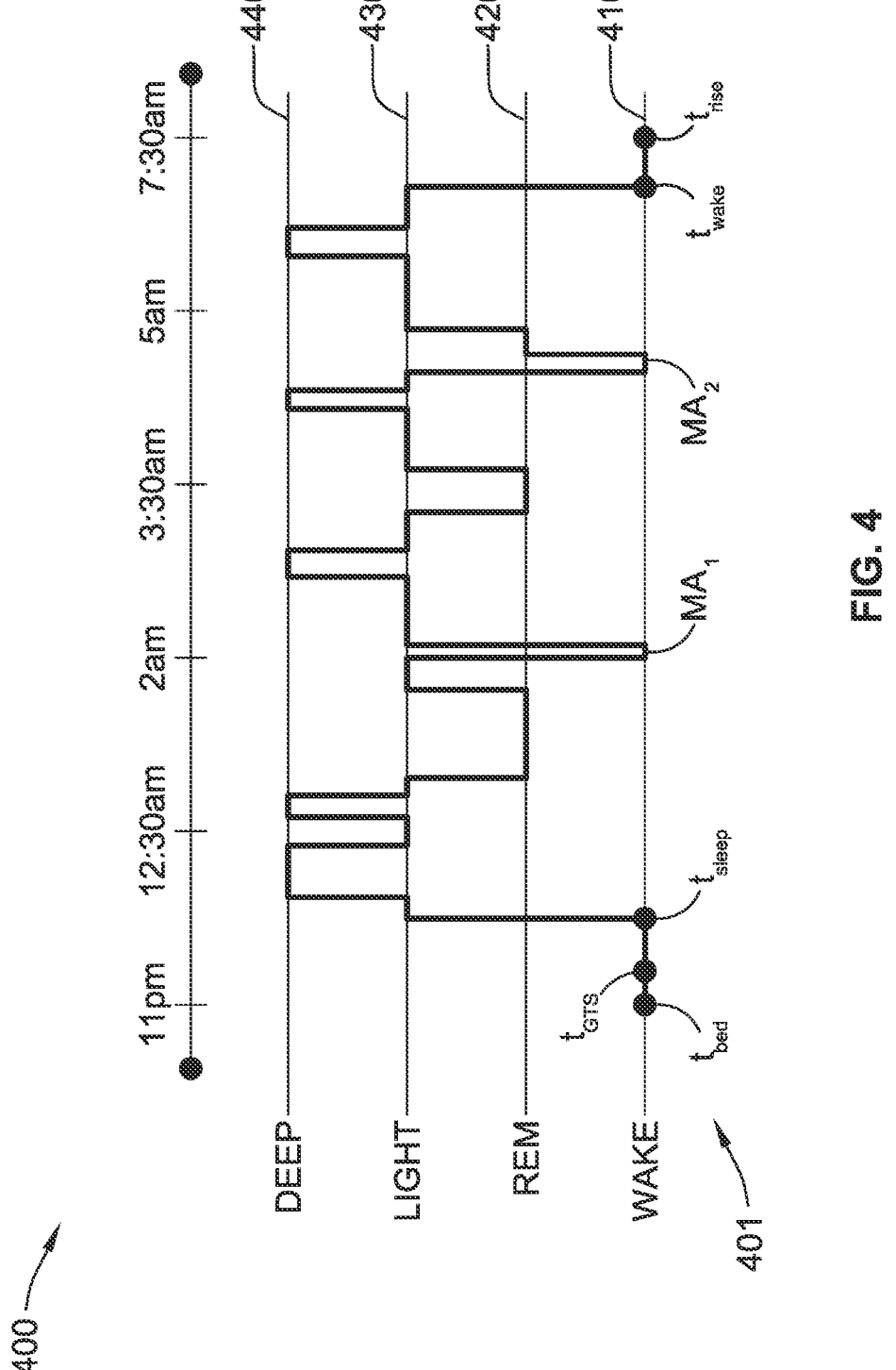
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based on physiological data associated with the user (e.g., generated by one or more of the sensors 130 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 114.

The hypnograph 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time (teed), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time teed can be determined based on, for example, data generated by the motion sensor 138, the microphone 140, the camera 150, or any combination thereof. The go-to-sleep time can be determined based on, for example, data from the motion sensor 138 (e.g., data indicative of no movement by the user), data from the camera 150 (e.g., data indicative of no movement by the user and/or that the user has turned off the lights) data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory therapy device 122, data indicative of the user donning the user interface 124, etc.), or any combination thereof.

Referring to FIG. 5, a method 500 for determining an activity score that is indicative of the effectiveness of an activity in modifying (e.g., increasing) the sleepiness of the user is illustrated. One or more steps of the method 500 can be implemented using any element or aspect of the system 100 (FIGS. 1-2) described herein.

Step 501 of the method 500 includes generating and/or receiving initial physiological data associated with a user. The initial physiological data can be received by, for example, the electronic interface 119 (FIG. 1) described herein. The initial physiological data can be generated or obtained by at least one of the one or more sensors 130 (FIG. 1). For example, in some implementations, the initial physiological data are generated using the acoustic sensor 141 or the RF sensor 147 described above, which are coupled to or integrated in the user device 170. In other implementations, the initial physiological data are generated or obtained using the pressure sensor 132 and/or the flow rate sensor 134 (FIG. 1), which are coupled to or integrated in the respiratory therapy device 122. Information describing the initial physiological data received during step 501 can be stored in the memory device 114 (FIG. 1).

Step 502 of the method 500 includes determining an initial sleepiness level for the user based at least in part on the initial physiological data (step 501). For example, the control system 110 can analyze the initial physiological data (e.g., that is stored in the memory device 114) to determine the initial sleepiness level for the user. Information describing the initial sleepiness level can be stored in the memory device 114 (FIG. 1), for example.

As used herein, a sleepiness level is generally indicative of the user's fatigue, drowsiness, alertness, and/or awareness, and more generally is indicative of how close the user is to falling asleep. The sleepiness level can be determined and/or expressed in a variety of ways. For example, a sleepiness level can be a scaled value within a predetermined range (e.g., between 1 and 10) where the highest value is indicative of being very sleepy and the lowest is indicative of not being sleepy (or vice versa). Alternatively, the sleepiness level can be expressed using a subjective descriptor (e.g., extremely sleepy, very sleepy, sleepy, neutral, awake, very awake, extremely awake, challenged, focused, fatigued, etc.). Other examples for expressing a sleepiness level include using the Epworth sleepiness scale, the Stanford sleepiness scale, the Karolinska sleepiness scale, etc. The multiple sleep latency test (MSLT) and the maintenance of wakefulness test (MWT) use objective measures to quantify sleepiness. The Oxford SLEep Resistance (OSLER) test, which is a simplified variation of the MWT, is another objective test that can be used to indirectly quantify sleepiness. The Epworth sleepiness scale and Stanford sleepiness scale subjectively quantify sleepiness.

The sleepiness level can be determined based on various types of data or combinations of data. In some implementations, a sleepiness level of a user can be determined based at least in part on physiological data associated with the user. For example, the sleepiness level can be based on a respiration rate, respiration rate variability, breathing stability (e.g., consistency of shape and/or rate of each breath, a mean squared difference between successive breaths), change in tidal volume (e.g., estimated from an amplitude of respiration), a movement associated with the user (e.g., physical movement of any portion of the user, chest movement of the user, etc.), eye blinking (e.g., a number of eye blinks per minute, an average of eye blinks per minute, etc.), duration of one or more of these parameters (e.g., sleepiness level may increase with increased duration of a predetermined breathing shaped, but decreases if movement of a portion of a user's body (e.g. if a user sits up in bed) is detected).

The sleepiness level can also be determined, for example, using an algorithm or statistical model, such as, for example, a linear regression algorithm, a logistic regression algorithm, a machine learning algorithm (e.g., supervised or unsupervised trained machine learning algorithm), a support vector machine algorithm (SVM), a decision tree, etc.). For example, a model (e.g., machine learning algorithm) can be trained to receive as an input data (e.g., physiological data, subjective feedback, scores from any of the objective sleepiness tests described herein, etc.) and predict a sleepiness level according one or more of the objective tests described herein (e.g., Epworth, Stanford, Karolinska, MSLT, MWT, OSLER, etc.). Such models can also use demographic information associated with the user to predict the sleepiness level. As an example, females may generally have a lower tidal volume (e.g., compared to males), or individuals with a high body mass index (BMI) may have larger tidal volume. Other data that can be used for predicting a sleepiness level include a typical sleep schedule of the user, a day of the week, a work schedule of the user, whether the user has been diagnosed with and/or has symptoms of insomnia, level of activity or exercise, caffeine and/or alcohol intake, etc. In some cases, the predicted sleepiness level may not match the subjective sleepiness level reported by the user. In such cases, the model (e.g. machine learning algorithm) for determining the sleepiness level can be modified or adjusted on a user-by-user basis.

In one example, the sleepiness level can be determined based on physiological data from the EEG sensor 158 (FIG. 1) described herein. In another example, the sleepiness level can be determined using data from the camera 150 (FIG. 1) to determine one or more properties of the eye(s) of the user that are indicative of sleepiness (e.g., measuring a vertical eye opening or eye height, opening of the eyes, closing of the eyes, blinking of the eyes, eye movement, pupil dilation, etc.). In yet another example, the sleepiness data can be determined based on a heart rate of the user, a heart rate variability of the user, a respiration rate of the user, a respiration rate variability of the user, a body temperature of the user, or any combination thereof.

In some implementations, step 502 includes receiving subjective feedback from the user and determining the initial sleepiness level based at least in part on the subjective feedback. The subjective feedback can include, for example, a self-reported subjective sleepiness level (e.g., tired, sleepy, average, neutral, awake, rested, etc.). Information associated with or indicative of the feedback from the user can be received, for example, through the user device 170 (e.g., via alphanumeric text, speech-to-text, etc.). In some implementations, the method 500 includes prompting the user to provide the feedback for step 502. For example, the control system 110 can cause one or more prompts to be displayed on the display device 172 of the user device 170 (FIG. 1) that provides an interface for the user to provide the feedback (e.g., the user clicks or taps to enter feedback, the user enters feedback using an alphanumeric keyboard, etc.). The received user feedback can be stored, for example, in the memory device 114 (FIG. 1) described herein.

In some implementations of the method 500, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia, an employment status of the user, an educational status of the user, a socioeconomic status of the user, or any combination thereof. The medical information can include, for example, including indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

Step 503 of the method 500 includes prompting the user to perform a first activity. In some implementations, the user can be prompted, for example, via the user device 170 (e.g., via text, audio, or both). In such implementations, the control system 110 can cause the user device 170 to prompt the user to perform the first activity. The first activity can be, for example, a mental activity, a physical activity, reading, a game, a puzzle, watching media content (e.g., a video, a movie, a television show, etc.), listening to audio content (e.g., an audiobook), exercise, movement (e.g., movement to expend energy, movement to induce fatigue, etc.), yoga, meditation, breathing exercises, consuming a beverage (e.g., warm milk), or any combination thereof. In some implementations, the user device 170 also provides or facilitates the first activity (e.g., via the display 172). The type/nature of the first activity may be selected based on, for example, the initial sleepiness of the user and the likelihood of the first activity modifying (e.g. increasing) the sleepiness of the user.

Step 504 of the method 500 includes receiving subsequent physiological data associated with the user in the same or similar manner as the initial physiological data received during step 501. The subsequent physiological data (step 504) differs from the initial physiological data (step 501) in that the subsequent physiological data are generated or obtained during at least a portion of the first activity, during the entire first activity, subsequent to the user performing the first activity, or any combination thereof. For example, the subsequent physiological data can be generated during the entirety of the first activity or a portion of the first activity (e.g., at least 10% of the first activity, at least 30% of the first activity, at least 50% of the first activity, at least 75% of the first activity, at least 90% of the first activity, etc.). The subsequent physiological data can be also generated or obtained after completion of the first activity (e.g., within about 30 seconds of completion of the first activity, within about 1 minute of completion of the first activity, within about 3 minutes of completion of the first activity, within about 10 minutes of completion of the first activity, within about 30 minutes of completion of the first activity, etc.).

Step 505 of the method 500 includes determining a subsequent sleepiness level for the user based at least in part on the subsequent physiological data (step 504). The subsequent sleepiness level can be determined in the same or similar manner as the initial sleepiness level (step 502) described herein. The subsequent sleepiness level differs from the initial sleepiness level in that the subsequent sleepiness level is indicative of the sleepiness of the user after having performed the first activity. For example, in at least some cases, the subsequent sleepiness level can be greater than the initial sleepiness level (e.g., the user is more tired after performing the first activity).

In some implementations, step 505 also includes receiving subjective feedback from the user and determining the subsequent sleepiness level based at least in part on the subjective feedback. The subjective feedback can include, for example, a self-reported subjective sleepiness level (e.g., tired, sleepy, average, neutral, awake, rested, etc.). Information associated with or indicative of the feedback from the user can be received, for example, through the user device 170 (e.g., via alphanumeric text, speech-to-text, etc.). In some implementations, the method 500 includes prompting the user to provide the feedback for step 505. For example, the control system 110 can cause one or more prompts to be displayed on the display device 172 of the user device 170 (FIG. 1) that provides an interface for the user to provide the feedback (e.g., the user clicks or taps to enter feedback, the user enters feedback using an alphanumeric keyboard, etc.). The received user feedback can be stored, for example, in the memory device 114 (FIG. 1) described herein.

Step 505 of the method 500 includes determining a first activity score indicative of the effectiveness of the first activity in modifying (e.g., increasing) the sleepiness of the user based at least in part on the initial sleepiness level (step 502), the subsequent sleepiness level (step 504), or both. The first activity score can be, for example, a numerical value that is on a predetermined scale (e.g., between 1-10, between 1-100, etc.), a letter grade (e.g., A, B, C, D, or F), or a descriptor (e.g., poor, fair, good, excellent, average, below average, etc.). The numerical value, letter grade or descriptor is assigned to an activity, and represents an activity score, based on how effective the activity is in inducing and/or increasing the sleepiness of a user. This numerical value, letter grade or descriptor can correspond to the activity being effective or not effective in inducing and/or increasing sleepiness, or a graduated effectiveness in inducing and/or increasing sleepiness which may be an absolute value assigned to the activity (e.g. on a predetermined scale) or a relative value assigned to an activity relative to other activities (e.g. other activities undertaken, or which may be undertaken, by the user). Generally, the first activity score is then associated with the first activity (e.g., in the memory device 114) to reflect how effective the first activity was in increasing the sleepiness of the user.

In some implementations, the first activity score is determined based at least in part on a difference between the initial sleepiness level (step 502) and the subsequent sleepiness level (step 505). For example, if the initial sleepiness level was a 5 on a scale of 1-10 and the subsequent sleepiness level was a 9 on the 1-10 scale, the first activity score can be determined as 4 based on the difference. In some implementations, the first activity score can be determined based at least in part on a rate of change between the initial sleepiness level (step 502) and the subsequent sleepiness level (step 505). In other implementations, the first activity score can be determined based at least in part on a predetermined threshold. For example, the first activity score can be determined based at least in on a difference between an initial time associated with the initial sleepiness level (step 502) and a second time associated with the subsequent sleepiness level that exceeds the predetermined threshold.

In some implementations, the method 500 includes prompting the user to perform a second activity in the same or similar manner as described in reference to step 503. In some implementations, the second activity is different than the first activity. The second activity can have, for example, a different complexity than the first activity (e.g., the second activity is less complex), a different duration than the first activity (e.g., the second activity is longer than the first activity), or both. Generally, the complexity of the activity can be associated with, for example, the level of attention required by the user to perform the activity, the level of input required from the user to perform the activity, the number of actions required by the user to perform the activity, the length of the activity, the duration of the activity, the speed of the activity, or any combination thereof. The complexity of the activity can be expressed with a subjective description (e.g., very difficult, difficult, easy, very easy, non-trivial, trivial, average, below average, above average, etc.). Alternatively, the complexity of the activity can be expressed as a value within a predetermined range (e.g., between 1 and 10, where 1 is the least complex and 10 is the most complex, or vice versa). In some implementations, the second activity is associated with a second activity score and is selected based on the first activity score (step 506) (e.g., the second activity score associated with the second activity is higher than the determined first activity score for the first activity).

In some implementations, the method 500 includes receiving information indicative of a reaction of the user in response to a provided stimulus. For example, the method 500 can include using a standardized test such as, for example, a click reaction time test, a tap reaction time test, a speed test, a recognition test, a resolution test, a processing test, a decoding test, a reaction stick test, a light board reaction test, or any combination thereof to provide a stimulus and receive information indicative of a reaction of the user to the stimulus (e.g., reaction time and/or reaction accuracy). In another example, the stimulus is generated by a light source (e.g., the display 172 of the user device 170 described herein). In further example, the stimulus is generated by a speaker (e.g., the speaker 142 described herein). In such implementations, step 505 includes determining the first activity score based at least in part on information indicative of the reaction of the user in response to the provided stimulus. The information indicative of the reaction of the user can include a reaction time, a reaction accuracy, or both. Information describing the reaction time can be used to determine the initial sleepiness level (step 502) and/or the subsequent sleepiness level (step 505).

In some implementations, the method 500 includes confirming the determined first activity score based at least in part on additional physiological data generated during a sleep session of the user that is subsequent to the first activity. In such implementations, the method 500 includes receiving sleep physiological data (e.g., generated by any combination of the sensors 130 described herein) associated with at least a portion of a sleep session of the user. The method can also include determining one or more of the sleep-related parameters described herein associated with the sleep session based at least in part on the sleep physiological data. The one or more sleep-related parameters can then be used to confirm or verify the determined first activity score (step 506). For example, the method can include determining a sleep-onset latency parameter for the sleep session subsequent to the first activity. If the sleep-onset parameter is less than a predetermined threshold (e.g., 15 minutes, 20 minutes, 30 minutes, etc.) and the first activity score is indicative of the first activity being effective in increasing the sleepiness of the user, the sleep-onset parameter can confirm the first activity is in fact effective in increasing the sleepiness of the user.

One or more of the steps of the method 500 described herein can be repeated one or more time for additional activities (e.g., a second activity, a third activity, a tenth activity session, etc.).

Referring to FIG. 6, a method for modifying one or more parameters of an activity to increase the sleepiness of the user is illustrated. One or more steps of the method 600 can be implemented using any element or aspect of the system 100 (FIGS. 1-2) described herein.

Step 601 of the method 600 is similar to step 501 of the method 500 (FIG. 5) described herein and includes receiving physiological data associated with a user. The physiological data can be received by, for example, the electronic interface 119 (FIG. 1) described herein. The physiological data can be generated or obtained by at least one of the one or more sensors 130 (FIG. 1). Information describing the physiological data received during step 601 can be stored in the memory device 114 (FIG. 1). Step 601 differs from step 501 of the method 500 (FIG. 5) in that step 601 includes receiving physiological data before, during, and/or after the first activity described in connection with step 603, as opposed to only physiological data prior to the performing of the first activity by the user.

Step 602 of the method 600 is the same as, or similar to, step 502 of the method 500 (FIG. 5) described herein and includes determining an initial sleepiness level for the user based at least in part on the received physiological data (step 501). For example, the control system 110 can analyze the physiological data (e.g., that is stored in the memory device 114) to determine the initial sleepiness level for the user. Information describing the initial sleepiness level can be stored in the memory device 114 (FIG. 1), for example.

Step 603 of the method 600 is the same as, or similar to, step 503 of the method 500 (FIG. 5) described herein and includes prompting the user to perform a first activity. In some implementations, the user can be prompted, for example, via the user device 170 (e.g., via text, audio, or both). In such implementations, the control system 110 can cause the user device 170 to prompt the user to perform the first activity. The first activity can be, for example, a mental activity, a physical activity, reading, a game, a puzzle, watching media content (e.g., a video, a movie, a television show, etc.), listening to audio content (e.g., an audiobook), exercise, movement (e.g., movement to expend energy, movement to induce fatigue, etc.), yoga, meditation, breathing exercises, consuming a beverage (e.g., warm milk), or any combination thereof. In some implementations, the user device 170 also provides or facilitates the first activity (e.g., via the display 172). The type/nature of the first activity may be selected based on, for example, the initial sleepiness of the user and the likelihood of the first activity modifying (e.g. increasing) the sleepiness of the user.

Step 604 of the method 600 includes determining a second sleepiness level for the user during a first portion of the first activity based at least in part on the physiological data (step 601). Step 604 is similar to step 504 of the method 500 (FIG. 5) described herein in that the second sleepiness level is determined after the user begins the first activity, but differs in that the second sleepiness level corresponds to only a first portion of the first activity. The first portion of the first activity can be, for example, at least about 10% of the total time of the first activity, at least about 25% of the total time of the first activity, at least about 33% of the total time of the first activity, at least about 50% of the total time of the first activity, at least about 75% of the total time of the first activity, etc. In some implementations, step 604 additionally includes determining a rate of change between the initial sleepiness level (step 602) and the second sleepiness level (step 604).

In some implementations, step 604 also includes determining one or more respiratory parameters associated with the user during the first portion of the first activity based at least in part on the physiological data (step 601). For example, the control system 110 can analyze the physiological data (e.g., that is stored in the memory device 114) to determine respiratory parameters. The one or more respiratory parameters can include, for example, a respiration rate, a respiration amplitude, a tidal volume change, an inspiration amplitude, an expiration amplitude, an inspiration-expiration ratio, or any combination thereof.

Step 605 of the method 600 includes modifying one or more parameters of the first activity for a second portion of the first activity based at least in part on the determined second sleepiness level (step 604) and/or the initial sleepiness level (step 602). The parameters of the first activity can include, for example, a complexity, a speed, a volume, a rhythm, a cadence, a music tempo, a brightness, a screen brightness, a font size, a font type, a color, or any combination thereof. Generally, the parameter(s) of the first activity can be modified so as to increase the effectiveness of the first activity in modifying (e.g., increasing) the sleepiness of the user as described herein. For example, if the first activity is displayed via the display device 172 of the user device 170, the screen brightness can be decreased and/or the color can be changed (e.g., to warmer colors, eliminating blue light, etc.) to cause less strain on the eyes of the user and aid in increasing the sleepiness of the user.

As described above, in some implementations, step 604 also includes determining one or more respiratory parameters associated with the. In such implementations, step 605 can include modifying the rhythm, the cadence, the music tempo, or any combination thereof for the second portion of the first activity based at least on the determined one or more respiratory parameters to aid in decreasing a respiration rate of the user. In some cases, the user's heartbeat and/or respiration rate can become substantially synchronized with music to which the user is listening. Thus, for example, if the first activity is audio content (e.g., music), the rhythm, cadence, and/or music tempo can be modified (e.g., slowed down) to lower the respiration rate and/or heart rate of the user to aid in increasing the sleepiness of the user.

As described above, in some implementations, step 604 additionally includes determining a rate of change between the initial sleepiness level (step 602) and the second sleepiness level (step 604). In such implementations, step 605 can include continuously modifying the one or more parameters of the first activity for the second portion of the first activity based at least in part on the determined rate of change between the initial sleepiness level and the second sleepiness level.

Referring to FIG. 7, a method 700 for determining one or more recommended activities to aid in modifying a sleepiness level of the user is illustrated. One or more steps of the method 700 can be implemented using any element or aspect of the system 100 (FIGS. 1-2) described herein.

Step 701 of the method 700 includes receiving first physiological data and second physiological data associated with a user from one or more sensors. The first and second physiological data can be received by, for example, the electronic interface 119 (FIG. 1) described herein. The first and second physiological data can be generated or obtained by at least one of the one or more sensors 130 (FIG. 1). For example, the first physiological data can be generated by a first sensor or first group of sensors of the sensors 130 described herein, while the second physiological data are generated by a second sensor or second group of sensors that is distinct from the first sensor or first group of sensors. The first physiological data and the second physiological data can be generated and/or received at different times. For example, the first physiological data can be generated and received prior to the second physiological data being generated and/or received. Information describing the first and second physiological data received during step 701 can be stored in the memory device 114 (FIG. 1).

Step 702 of the method 700 includes accumulating, in a user profile associated with the user, historical sleepiness data for the user including a set of previously recorded changes in sleepiness level for the user, each one of the changes in sleepiness level in the set of previously recorded changes in sleepiness level being associated with a corresponding one of a plurality of activities, the historical sleepiness data being based at least in part on the first physiological data.

The user profile can also include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia, an employment status of the user, an educational status of the user, a socioeconomic status of the user, or any combination thereof. The medical information can include, for example, including indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

Step 703 of the method 700 is the same as, or similar to, step 502 of the method 500 (FIG. 5) described herein and includes determining an initial sleepiness level for the user based at least in part on the second physiological data (step 701).

Step 704 of the method 700 includes training an algorithm using the user profile such that the algorithm is configured to (i) receive as an input the initial sleepiness level of the user (step 703) and (ii) determine as an output one or more recommended activities from the plurality of activities to aid in modifying the sleepiness level of the user relative to the initial sleepiness level. The algorithm can be, for example, a machine learning algorithm, (e.g., supervised or unsupervised) or a neural network (e.g., shallow or deep approaches). The algorithm can be trained using data from the user profile data (step 702) and/or other data sources (e.g., data associated with other individuals besides the user).

In some implementations, the method 700 also includes communicating information indicative of the recommended activity or activities to the user (e.g., using the user device 170 (FIG. 1) described herein). In other implementations, the method 700 can include automatically starting or launching the recommended activity or activities on the user device 170 subsequent to step 704.

Referring to FIG. 8, a method 800 for calibrating a sensor for determining a sleepiness level of a user is illustrated. One or more steps of the method 800 can be implemented using any element or aspect of the system 100 (FIGS. 1-2) described herein.

Step 801 of the method 800 includes generating first physiological data associated with a user during a first period using a first sensor. In some implementations, the first sensor is the EEG sensor 158 (FIG. 1) described herein. In some implementations, the first sensor is the PPG 154 (FIG. 1) described herein. The first physiological data can be received by, for example, the electronic interface 119 (FIG. 1) described herein. Information describing the first physiological data received during step 801 can be stored in the memory device 114 (FIG. 1).

Step 802 of the method 800 includes generating second physiological data associated with the user during the first period using a secondary sensor. The secondary sensor is different than the first sensor used during step 801. In some implementations, the secondary sensor is one of the sensors 130 (or a combination thereof) and is coupled to or integrated in the user device 170 and/or the respiratory therapy system 120 (FIG. 1). The second physiological data can be received by, for example, the electronic interface 119 (FIG. 1) described herein. Information describing the second physiological data received during step 802 can be stored in the memory device 114 (FIG. 1).

Step 803 of the method 800 includes determining a first sleepiness level of the user based on the first physiological data generated by the first sensor. The first sleepiness level can be determined by, for example, the control system 110 (FIG. 1) described herein.

Step 804 of the method 800 includes determining a second sleepiness level of the user based on the second physiological data generated by the secondary sensor. The second sleepiness level can be determined by, for example, the control system 110 (FIG. 1) described herein.

Step 805 of the method 800 includes calibrating the secondary sensor such that the determined second sleepiness level matches the determined first sleepiness level. As described above, in some implementations, the first sensor can be the EEG sensor 158 (FIG. 1) described herein. The EEG sensor 158 often includes one or more electrodes that are placed on the head of the user to monitor electrical activity in the brain. Thus, physiological data from the EEG sensor 158 can be used to determine an accurate sleepiness level of the user based on the brain activity of the user. However, the EEG sensor 158 is cumbersome due the placement of electrodes and is therefore not suitable for practical, everyday personal use.

The secondary sensor, by contrast, generates different physiological data for the user from which the sleepiness level of the user can be determined. However, because the secondary sensor is not directly measuring brain activity, the determined sleepiness level may not be as accurate as using the EEG sensor 158. Thus, step 805 includes calibrating the secondary sensor such that the sleepiness level determined based on data from the secondary sensor is substantially equal to (e.g., within 90% accuracy, within 92% accuracy, within 95% accuracy, etc.) of the sleepiness level determined based on data from the first sensor.

Figure 9:
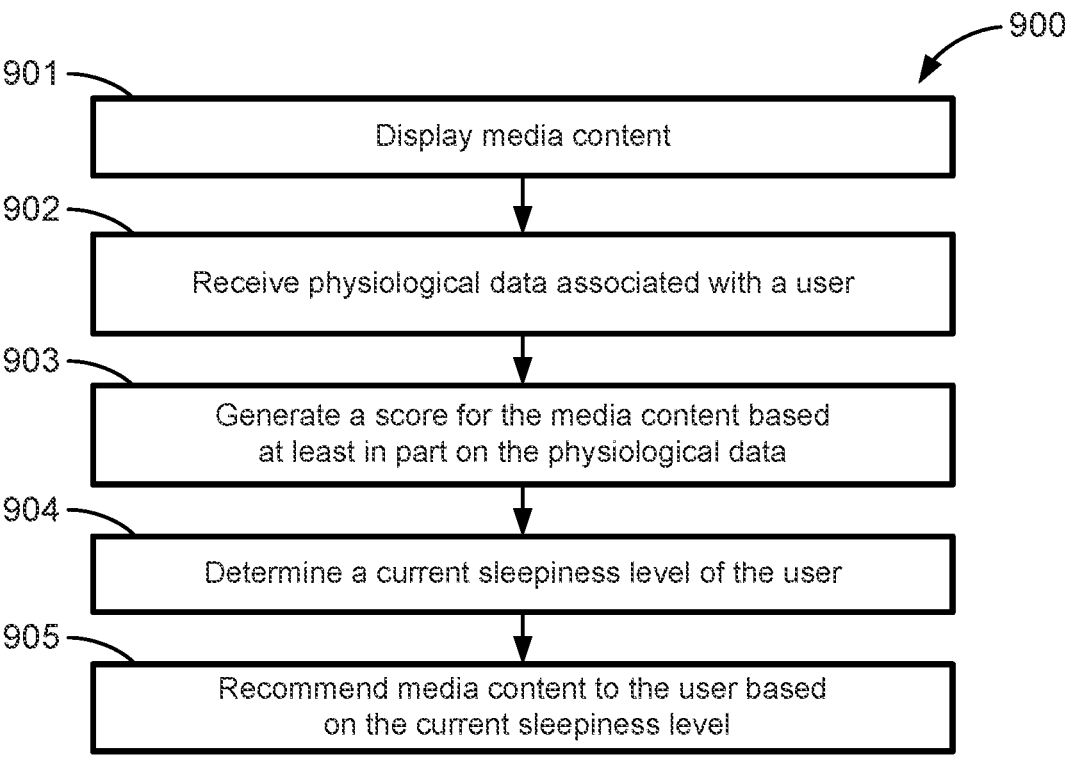
FIG. 9 is a process flow diagram for recommending media content to a user based on the current sleepiness level of the user, according to some implementations of the present disclosure.

Referring to FIG. 9, a method 900 for recommending media content to a user based on the current sleepiness level of the user is illustrated. One or more steps of the method 900 can be implemented using any element or aspect of the system 100 (FIGS. 1-2) described herein.

Step 901 of the method 900 includes displaying media content to a user. The media content can be displayed, for example, using the display device 172 of the user device 170 (FIG. 1) described herein. The media content or can include, for example, video content, audio content, a television show, a movie, a documentary, a video game session, document review session, a program, or any combination thereof. The media content can generally include a plurality of media content segments. For example, a first media content segment can be a first television show episode and a second media content segment can be a second television show episode.

Step 902 of the method 900 includes receiving physiological data associated with the user while the user views the displayed media content. The physiological data can be received by, for example, the electronic interface 119 (FIG. 1) described herein. The physiological data can be generated or obtained by at least one of the one or more sensors 130 (FIG. 1). For example, the physiological data can be generated by a sensor or group of sensors of the sensors 130 described herein that is coupled to or integrated in the user device 170. Information describing the physiological data received during step 901 can be stored in the memory device 114 (FIG. 1).

Step 903 of the method 900 includes generating a score that is for the media content or for one or more of the plurality of media content segments based at least in part on the generated data associated with the user. For example, the control system 110 can analyze the physiological data (e.g., that is stored in the memory device 114) to determine the score for the media content. Similar to the activity scores described herein (e.g., in connection with step 506 of the method 500), the score is generally indicative of the effectiveness of the media content in modifying (e.g., increasing) the sleepiness level of the user. For example, if the media content is a fast-paced action movie, the media content may make the user more alert or attentive and decrease the sleepiness level of the user. By contrast in another example, if the media content is something less likely to hold the user's interest (e.g., a television show the user has seen, a documentary, etc.), that media content can increase the sleepiness level of the user. The determined score is indicative of the ability of the media content to change the sleepiness level of that particular user. Information describing the score(s) for the media content or media content segments can be stored in the memory device 114 (FIG. 1), for example.

Step 904 of the method 900 includes determining a current sleepiness level of the user based at least in part on current physiological data for the user. Step 904 is the same as, or similar to, for example, step 502 of the method 500 (FIG. 5) described herein.

Step 905 of the method 900 includes recommending media content to the user based at least in part on the current sleepiness level of the user to aid in changing the current sleepiness level of the user. For example, step 905 can include recommending one of a plurality of media content segments which is associated with a score as described above in step 903. Thus, if the initial sleepiness level is low (e.g., the user is not close to falling asleep), step 905 can include recommending media content with an associated score that is indicative of the media content being more effective in decreasing the sleepiness level of the user. The recommended media content can be determined by the control system 110 (FIG. 1), for example.

In some implementations, step 905 includes recommending a plurality of successive media content segments. For example, step 905 can include recommending a first media content segment (e.g., a television show episode) with a first score, then a second media content segment (e.g., a different television show episodes) with a second score. The two segments can be displayed to the user in sequence so that the effect of the two segments is to gradually increase the sleepiness level of the user relative to the initial sleepiness level.

In some implementations, the method 900 includes communicating information indicative of the recommendation (step 905) to the user. For example, the recommendation can be communicated to the user via the user device 170 (e.g., via alphanumeric text, audio, etc.). Alternatively, the method 900 can include automatically displaying the recommended media content to the user (e.g., the control system 110 automatically causes the user device 170 to display the recommended media content to the user).

One or more elements or aspects or steps, or any portion(s) thereof, from one or more of any of the claims below can be combined with one or more elements or aspects or steps, or any portion(s) thereof, from one or more of any of the other claims combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system comprising:
a memory storing machine-readable instructions; and
a control system including one or more processors configured to execute the machine-readable instructions to:
receive initial physiological data associated with a user, the initial physiological data being generated by a sensor;
determine, based at least in part on the initial physiological data, an initial sleepiness level for the user, wherein the initial sleepiness level is indicative of how close the user is to falling asleep;
based at least in part on the initial sleepiness level, cause an electronic device to provide the user with a first portion of an activity, in which the activity is presented by the electronic device and is performed by the user interacting with the electronic device, the first portion of the activity having a plurality of device-based parameters associated therewith pertaining to how the electronic device visually or audibly outputs the activity to the user;
receive subsequent physiological data associated with the user, the subsequent physiological data being generated by the sensor while the user is performing the first portion of the activity, after the user has performed the activity, or both;
determine, based at least in part on the subsequent physiological data, a subsequent sleepiness level for the user;
determine a first activity score based at least in part on the initial sleepiness level and the subsequent sleepiness level, the first activity score being indicative of an effectiveness of the first portion of the activity in modifying the sleepiness of the user;
based at least in part on the first activity score, modify at least one of the plurality of device-based parameters of the first portion of the activity for use in a second portion of the activity; and
cause the electronic device to provide the user with the second portion of the activity to be performed by the user interacting with the electronic device.

2. The system of claim 1, wherein the first activity score is determined based at least in part on a difference between the initial sleepiness level and the subsequent sleepiness level.

3. The system of claim 1, wherein the first activity score is determined based at least in part on a rate of change between the initial sleepiness level and the subsequent sleepiness level.

4. The system of claim 1, wherein the control system is further configured to determine whether the subsequent sleepiness level exceeds a predetermined threshold.

5. The system of claim 4, wherein the control system is further configured to determine the first activity score based at least in part on a difference between an initial time associated with the initial sleepiness level and a second time associated with the subsequent sleepiness level exceeding the predetermined threshold.

6. The system of claim 1, wherein the control system is further configured to display the prompt on the electronic device for the user to perform a second activity based at least in part on the first activity score.

7. The system of claim 6, wherein (i) a complexity of the second activity is less than a complexity of the activity, (ii) a duration of the second activity is greater than a duration of the activity, (iii) or both (i) and (ii).

8. The system of claim 1, wherein the activity, a second activity, or both includes a game via the electronic device, a puzzle via the electronic device, reading via the electronic device, watching a video via the electronic device, listening to audio content via the electronic device, or any combination thereof.

9. The system of claim 1, wherein the control system is further configured to:
receive information indicative of a reaction of the user in response to a provided stimulus; and
determine the activity score based at least in part on the information indicative of the reaction of the user in response to the provided stimulus.

10. The system of claim 9, wherein the information indicative of the reaction of the user includes a reaction time, a reaction accuracy, or both.

11. The system of claim 1, wherein the sensor includes an EEG sensor, an acoustic sensor, a camera, a motion sensor, an infrared sensor, or any combination thereof.

12. The system of claim 1, wherein the initial physiological data, the subsequent physiological data, or both is indicative of opening of eyes of the user, closing of the eyes of the user, blinking of the eyes of the user, pupil dilation of the eyes of the user, a body temperature of the user, head movement of the user, heart rate of the user, a heart rate variability of the user, a respiration rate of the user, or any combination thereof.

13. The system of claim 1, wherein the control system is further configured to receive third physiological data associated with the user for a sleep session that is subsequent to the user performing the activity.

14. The system of claim 13, wherein the control system is further configured to determine one or more sleep-related parameters associated with the user for the sleep session based at least in part on the third physiological data, and confirm the first activity score based at least in part on the one or more sleep-related parameters.

15. The system of claim 14, wherein the one or more sleep-related parameters includes a sleep onset latency parameter.

\*　\*　\*　\*　\*